US006458388B1

(12) United States Patent
Genis et al.

(10) Patent No.: US 6,458,388 B1
(45) Date of Patent: Oct. 1, 2002

(54) COSMETIC CREAM CONTAINING GRANULAR COMPONENTS AND METHOD FOR MAKING IT

(75) Inventors: Margarita Genis, Arad; Izhak Haliva, Beer-Sheva; Shaul Zolotov, Lehavim, all of (IL)

(73) Assignee: Dead Sea Works, Ltd., Beer-Sheva (IL)

( * ) Notice: Subject to any disclaimer, the term of this patent is extended or adjusted under 35 U.S.C. 154(b) by 0 days.

(21) Appl. No.: 09/574,402

(22) Filed: May 19, 2000

Related U.S. Application Data

(63) Continuation of application No. PCT/IL98/00565, filed on Nov. 19, 1998.

(30) Foreign Application Priority Data

Nov. 20, 1997 (IL) .................................. 122256
Nov. 20, 1997 (IL) .................................. 122257

(51) Int. Cl.⁷ ............................ A61K 7/48; A61K 7/02; A61K 7/40; A61K 7/50
(52) U.S. Cl. ...................... 424/489; 424/401; 424/400; 514/844; 514/845; 514/846; 514/847; 514/848
(58) Field of Search ................................ 424/489, 401, 424/400; 514/844, 845, 846, 847, 848

(56) References Cited

U.S. PATENT DOCUMENTS 3,944,506 A * 3/1976 Hramchenko et al. ...... 252/526
4,767,741 A 8/1988 Komor et al.

FOREIGN PATENT DOCUMENTS

| FR | 2 240 716 | | 3/1975 |
|---|---|---|---|
| GB | 815 338 | | 6/1959 |
| GB | 1479199 A | * | 7/1977 |

* cited by examiner

*Primary Examiner*—Thurman K. Page
*Assistant Examiner*—Rachel M. Bennett
(74) *Attorney, Agent, or Firm*—Anderson Kill & Olick; Eugene Lieberstein; Michael N. Meller

(57) ABSTRACT

The invention provides cosmetic creams containing granular components for cleansing and scrubbing the skin, which contain granules of a salt, in particular sodium or potassium chloride, and which are stable under storage and use conditions. In an embodiment of the invention, no rinsing is required after use. The invention also provides a process for making the cosmetic creams by mixing a solution of a salt, in the amount contained by a solution that is saturated at a temperature not lower than room temperature, with the water soluble ingredients of the cream base, emulsifying the mixture with the components of the oily phase of the cream base to obtain a complete mixture, homogenizing and cooling the complete mixture, adding fragrances and preservatives and optionally additives, and finally adding solid salt particles while continuing to homogenize said mixture.

19 Claims, No Drawings

COSMETIC CREAM CONTAINING GRANULAR COMPONENTS AND METHOD FOR MAKING IT

This application is a continuation of PCT/IL98/00565 filed Nov. 19, 1998.

FIELD OF THE INVENTION

This invention relates to cosmetic creams containing granular components, useful for cleansing and scrubbing the skin. It particularly relates to such creams which contain granules of a salt, in particular sodium or potassium chloride and which are stable under storage and use conditions. It further relates to such creams that are soluble in water and do not require mechanical removal after use.

BACKGROUND OF THE INVENTION

Cosmetic creams which contain solid particulate components are known in the art. The presence of the solid particles renders them useful for scrubbing and cleansing the skin, particularly of the face. Certain creams of such a kind contain polyethylene spherules, which are inert and insoluble and must removed from the user's skin, after application of the cream, by sufficiently intensive rinsing. Other creams, also known in the art, contain sodium chloride granules. They do not require such intensive rinsing, but have the drawback that the granules tend to dissolve in the water phase, and disappear during the storage of the cream and in the period of their use, so that the cream loses the desired properties. Further, such creams do not have a water phase, and are heavy on spreading on the skin. Still further, their preparation is not an easy process, because the addition of salts to creams, which generally comprise more than 50% of water, generates an aqueous solution of the salt, which is difficult to emulsify with the oily cream bases and often affects the physical properties of the resulting emulsion in an undesirable manner. In general, the complex nature of these emulsions of an aqueous and a non-aqueous phase creates manufacturing problems and deterioration of the properties of the resulting product, which the art has so far been unable to overcome.

It is therefore a purpose of this invention to provide a cosmetic cream which comprises salt granules and which is stable in storage and in use and does not lose its properties, and is therefore adapted for scrubbing, massaging and cleansing the skin.

It is another purpose of this invention to provide such a cosmetic cream which contains salt granules which will not dissolve and disappear with storage.

It is a further purpose of this invention to provide such a cosmetic cream which does not require rinsing, or at least not an immediate rinsing, after application.

It is a still further purpose of this invention to provide a cosmetic cream the use of which produces a particularly pleasant feeling.

It is still further purpose of this invention to provide such a cosmetic cream which contains granules of potassium salts.

It is a still further purpose of this invention to provide such a cosmetic cream which contains a plurality, up to even all, of the minerals of the Dead Sea.

It is a still further purpose of this invention to provide such a cosmetic cream which contains mixtures of granules of different salts.

It is a still farther purpose of this invention to provide such a cream which is easy to spread on the skin and has all the physical properties required for this purpose.

It is a still further purpose of this invention to provide a method of making a cosmetic cream, containing salt granules, for scrubbing and cleansing the skin, which method permits to impart to the cream the desired physical properties.

It is a still further purpose of this invention to provide such a method which permits to disperse in the cream salt granules that are stable and are not affected by storage of the cream.

It is a still further object of this invention to provide such a method which permits to prepare cosmetic creams containing granules of water-soluble salts other than sodium chloride.

It is a still further object of the invention to provide scrubbing creams in which the salt granules substantially completely dissolve after application, as a result of the scrubbing action, so that, after use, practically no granules are left on the skin and no rinsing, at least no immediate rinsing, is required and penetration of the salts into the skin is enhanced.

Other purposes and advantages of the invention will appear as the description proceeds.

SUMMARY OF THE INVENTION

The cosmetic cream according to the invention is characterized in that it contains at least a solid salt in the form of granules and an aqueous solution containing at least the same salt in such an amount as to become saturated with respect to said salt at a temperature not lower than room temperature.

In an embodiment of the invention, said solution becomes saturated with respect to said salt at a temperature higher than room temperature and preferably not lower than about 40° C.

In another embodiment of the invention, said solution becomes saturated with respect to said salt at or about room temperature, and preferably at a temperature of about 25° C.

The word "salt" is used in this specification and claims in its broad chemical meaning, and not as a common word to designate sodium chloride. The word "granules" means small solid particles and does not imply any limitation as to the shape of such particles nor as to their structure, though salt granules will generally have a crystalline structure.

In an embodiment of the invention, the aqueous solution contains a single salt as the sole minerals solute. In another embodiment, it contains a combination of Dead Sea salts as minerals solute.

In a preferred form of the invention, the salt granules are in an amount comprised between 3 and 15% and preferably between 5 and 10 % of the total cream All the percentages in this specification and claims are by weight, unless otherwise specified.

Preferably, the maximum linear dimension of the salt granules is 0.1–0.3 mm.

The salt is preferably sodium chloride or potassium chloride.

In a form of the invention, the cream also contains mixtures of mineral salts, particularly a mixture sold by Dead Sea Works Ltd. under the trade name DHB 400. A typical analysis of the aforesaid DHB 400 mixture is shown in Table I below.

TABLE I

| Component | Range (μg per ml) |
| --- | --- |
| Chloride | 324,000–338,000 |
| Magnesium | 105,000–111,000 |
| Sulphate | 100–150 |
| Potassium | 1,200–2,500 |
| Sodium | 2,000–3,000 |
| Calcium | 6,000–7,000 |
| Bicarbonate | 300–500 |
| Lithium | 7–11 |
| Boron | 15–25 |
| Nitrogen as Ammonia | 10–20 |
| Fluoride | 1–2 |
| Aluminium | 2–5 |
| Silicon | 1.5–2.0 |
| Manganese | 1.5–2.0 |
| Iron | 0.5–1.5 |
| Copper | 0.05–0.1 |
| Zinc | 0.3–0.5 |
| Bromide | 5,000–7,000 |
| Rubidium | 1–2 |
| Strontium | 100–110 |
| Barium | 1–2 |
| ρ (specific gravity) | 1.33–1.36 |

The cosmetic scrub creams in this invention refers are emulsions of an aqueous phase and an oily phase to which the solid salt is added. The oily phase plus the aqueous phase, plus the additives, fragrance and preservatives, other than the solid salt, will be called hereinafter "the cream base". The conventional prior art cosmetic creams, without added salt, are therefore basically emulsions of the cream base of this invention and water. The cosmetic creams of this invention contain water preferably in an amount of at least about 30% of the cream base or of the total of water and the cream base.

Therefore they contain 5 to 40 parts of salt, partly as granules and partly dissolved, 40 to 60 parts of cream base, and 30 to 50 parts of water. All parts in this specification and claims are by weight.

The process for preparing a cosmetic cream according to the invention comprises, in any suitable order, the steps of:

1—mixing a solution containing at least a salt in the amount-contained by a solution that is saturated at a first temperature not lower and preferably higher than room temperature, with the water soluble ingredients of the cream base;

2—emulsifying said solution with the components of the oily phase of the cream base at a second temperature, higher than said first temperature, to obtain a complete mixture;

3—homogenizing the two phases and concurrently cooling the complete mixture;

4—when a third temperature higher than room temperature has been reached, adding the DHB solution to the mixture, while continuing to homogenize said mixture, until room temperature is reached;

5—adding fragrances and preservatives;

6—mixing additives; and

7—adding solid salt particles while continuing to homogenize said mixture.

Of course, some steps, e.g. steps 5 and 6, can be unified into a single step, as will be apparent to the skilled person.

The salt or salts, to the solution of which step 1 of the process refers, and which is added as a solid in step 7, is the salt or salts which is to be contained in the form of granules on the cosmetic cream. The additives, that may be optionally added, can be chosen by skilled persons as desired for any particular cosmetic formulation. Examples are given hereinafter.

"Room temperature" means herein the temperature at which the cream is expected to be used, and, at any rate, a temperature comprised between 18° and 32° C. A typical room temperature is 25° C. Said first temperature is preferably higher than room temperature by 10°–20° C., typically by 15° C. Said second temperature is considerably higher than said first temperature, e.g. is 75–80° C. Said third temperature is preferably higher than room temperature by 10–20° C., typically by 15° C. It should be understood that said solution may be prepared at said first temperature or at a higher temperature.

In a preferred manner of carrying out step 1 of the process, the salt solution is mixed firstly with the water-soluble components of the cream base to obtain a first partial e. The oily components—"oily" meaning herein "liquid or solid and not mixable with water"—of the cream base are separately mixed to obtain a second partial mixture. Then said first and second partial mixtures, plus the additives, fragrance and preservatives, are mixed together to form what will be called herein "the complete mixture". Preferably, all these mixing operations are carried out at the temperatures specified hereinbefore.

In a preferred manner of carrying out step 7 of the process, the solid salt granules are slowly added to the complete mixture and, during said addition, the homogenization operation is continued under milder mechanical conditions, e.g. at a reduced speed of rotation if a rotary mixer is used, until a satisfactory homogeneity has been achieved.

In a preferred embodiment of the invention, a liquid mixture of salts, e.g. the aforesaid DHB 400 mixture, is added in step 4 of the process to the complete mixture, before adding the salt in granule form.

DETAILED DESCRIPTION OF PREFERRED EMBODIMENTS

The following examples illustrate the invention and are not intended to limit it in any way.

EXAMPLE 1

The cosmetic cream of this Example is prepared from the ingredients listed in Table II.

TABLE II

| No. | Formula | % |
| --- | --- | --- |
| 1 | Myvaplex 600p GMS S/E | 6.39 |
| 2 | Cithrol GMS A/S ES0 7 43 | 2.13 |
| 3 | Drakeol 9 | 10.25 |
| 4 | Isoprophyl myristrate | 10.25 |
| 5 | SF 18 (350) | 1.93 |
| 6 | Saturated solution of KCl at 40° C. (28%) or NaCl at 40° C. (24%) | 37.28 |
| 7 | DHB 400 | 5.86 |
| 8 | Propylene glycol | 14.91 |
| 9 | Fragrance | 0.2 |
| 10 | Preservative | 0.2 |
| 11 | Vitamin E acetate | 0.3 |
| 12 | Crilet super | 0.5 |
| 13 | KCl or NaCl (149μ–177μ) | 9.8 |

The various components are commercial components well known in the art.

Ingredients Nos. 1 to 12 constitute the cream base. Ingredient No. 13 is the salt according to the invention. The salt can be, as indicated in the table, either potassium chloride or sodium chloride, and have dimension 0.1–0.3 mm, e,g, 0.2 mm.

In order to make the cream, the salt solution ingredient No. 6 is mixed with ingredient No. 8, to form what is called herein mixture B and is a part of the water-soluble components of the cream base, at the first temperature. 40° C. is the preferred first temperature. The second temperature is between 75° and 80° C. A second mixture, which is an oily solution, is obtained by heating to 80° C. and mixing ingredients Nos. 1,2,3,4 and 5, which are not water-soluble, but are mixable together and are therefore the oily components which form what is called herein mixture A.

The two solutions-mixtures A and B-are mixed at the aforesaid temperature of 80° C., and the resulting mixture is homogenized in a beaker with a Heidolph DIAX. homogenizer at 8000 rpm while maintaining the temperature constant at the aforesaid second temperature value, for 10 minutes. Since the mixture tends to heat spontaneously during mixing, cooling may have to be employed to prevent the temperature from rising. Thereafter, the emulsion, which has formed from the two phases, is slowly cooled to 45° C., while continuing to homogenize it, till the emulsion is at about 45° C. At this point, ingredient number 7 is heated to 45° C. and added. The speed of the homogenizer is decreased and its operation is continued until a cream is cooled and obtained at room temperature.

In stage 5 of the process, the emulsion is cooled to 30° C., and ingredients 9 and 10 are added to the emulsion and homogenized at 2000 rpm, resulting in a complete mixture.

In stage 6 additives, such as e.g. ingredients 11 and 12, are mixed to produce the cream base.

Finally, in stage 7 of the process, the salt granules of sodium or potassium chloride, of the size hereinbefore specified, are added, preferably at room temperature, to the complete mixture, while the homogenizing operation is continued slowly. The amount of granules is 5–15% of the entire cream composition, including the salt solution.

In the aforesaid example, as in all embodiments of the invention, the presence of salt granules does not adversely affect the properties of the cream. The salt granules are stable and do not disappear during storage, no matter how prolonged. The presence of stable salt granules, during the use of the cream at room temperature, imparts to the cream its properties as a cleansing and scrubbing cream. The fact that the cream contains as a component, and in fact its major component, a solution of a salt, far from being harmful, is considered beneficial, particularly in the case of potassium salts and magnesium salts. The solid salt which remains on the skin can be rinsed off quite easily, since it is water-soluble. However, if ease of rinsing is not a major consideration, insoluble particles, such as polyethylene spherules, can be added to the cream, particularly when it contains DHB 400.

EXAMPLE 2

The cosmetic cream of this Example is prepared from the ingredients listed in Table III.

TABLE III

| No. | Formula | % |
|---|---|---|
| 1 | Myvaplex 600p GMS S/E | 7.06 |
| 2 | Cithrol GMS A/S ES0 7 43 | 2.35 |

TABLE III-continued

| No. | Formula | % |
|---|---|---|
| 3 | Drakeol 9 | 12.36 |
| 4 | Isoprophyl myristrate | 11.18 |
| 5 | SF 18 (350) | 1.77 |
| 6 | Saturated solution of KCl at 15° C. (24%) | 34.13 |
| 7 | DHB 400 | 17.66 |
| 8 | Propylene glycol | 7.49 |
| 9 | Fragrance | 0.2 |
| 10 | Preservative | 0.2 |
| 11 | Vitamin E acetate | 0.3 |
| 12 | Crilet super | 0.5 |
| 13 | KCl ($105\mu$–$149\mu$) | 9.8 |

The same operations are carried out as in Example 1, but DHB 400 is added to the complete mixture of salt solution and cream base after the homogenization at the second temperature has been carried out, during the cooling to 40° C. The addition of DHB 400 occurs, therefore, before that of the salt, which in this example is potassium chloride. This has been found to be preferable to avoid difficulties in the preparation of the cream. In fact, the emulsion has already formed before the DHB 400 has been added, and it is not damaged by the addition of the viscous solution In this example too the presence of salt granules does not adversely affect the properties of the cream. The salt granules are stable and do not disappear during storage, at least as long as the temperature of the storage does not significantly exceed room temperature. Some salt will crystallize from the solution when the cream is stored and/or used at temperatures that are below its saturation temperature, so that the amount of solid salt in the cream is slightly higher than the amount which has been added in preparing the cream. The presence of salt granules, during the use of the cream at room temperature, imparts to the cream its properties as- a cleansing scrubbing and massaging cream. However, the cream temperature rises because of contact with the skin, that is massaged and therefore slightly heated. This causes the aqueous phase of the cream to become unsaturated and part of the salt granules to dissolve into it. Further, some sweat is always exuded from the skin and it too contributes to the dissolution of all the salt granules, so that, after use, practically no granules are left on the skin and no rinsing, at least no immediate rinsing, is required and penetration of the salts into the skin is enhanced. As a result, the use of the cream generates a particularly pleasant and restful feeling, rendering the creams of this invention particularly desirable.

While some embodiments of the invention have been described by way of illustration, it will be apparent that the invention can be carried out by persons skilled in the art with many modifications, variations and adaptations, without departing from its spirit or exceeding the scope of the claims.

What is claimed is:

1. Cosmetic cream in the form of solid granules and an aqueous solution containing at least the same salt and saturated with respect to said salt at a temperature not lower than room temperature containing at least the salt potassium chloride.

2. Cosmetic cream according to claim 1, containing mixtures of salts.

3. Cosmetic cream according to claim 1, which is an emulsion of an aqueous phase and an oily phase, to which a solid salt is added.

4. Cosmetic cream according to claim 3, which contains 5 to 40 parts of salt, partly as granules and partly dissolved, 40 to 60 parts of cream base and 30 to 50 parts of water.

5. Process for preparing a cosmetic cream, which comprises, in any suitable order, the steps of:
- I—preparing a solution of at least a salt, that is saturated at a first temperature not lower than room temperature;
- II—mixing said solution with all the oily components of the cream base, as hereinbefore defined, at a second temperature, higher than said first temperature, to obtain a complete mixture;
- III—homogenizing and concurrently cooling the complete mixture thus obtained;
- IV—when a third temperature, higher than room temperature, has been reached, adding the "said salt" solution;
- V—adding fragrance and preservative;
- VI—mixing additives to form a complete mixture; and
- VII—adding solid salt particles while continuing to homogenize said complete mixture, until room temperature is reached.

6. Process according to claim 5, wherein the first temperature is higher than room temperature by 10° C.–20° C.

7. Process according to claim 6, wherein the first temperature is about 40° C.

8. Process according to claim 5, wherein the second temperature is about 75–80° C.

9. Process according to claim 5, wherein the third temperature is higher than room temperature by 10–20° C.

10. Process according to claim 9, wherein the third temperature is about 45° C.

11. Process according to claim 5, comprising:
- a—mixing the salt solution with the water-soluble components of the cream base to obtain a first partial mixture;
- b—separately mixing the oily components of the cream base to obtain a second partial mixture;
- c—mixing together said first and second partial mixtures are to form a cream mixture;
- d—mixing the cream mixture with additives fragrance and preservatives; and
- e—adding, when the third temperature has been reached, the salt in granule form, while continuing to homogenize said m e until room temperature is reached.

12. Process according to claim 11, wherein all the mixing are carried out at the same temperature.

13. Process according to claim 12, wherein all the mixing are carried out at the second temperature.

14. Process according to claim 5, wherein the salt solution is mixed with the oily components of the cream base at temperatures of about 75–80° C.

15. Process according to claim 5, wherein a mixture of salt solution is added to the mixture when the third temperature has been reached and before adding the salt in granule form.

16. Process for preparing a cosmetic cream, which comprises the steps of:
- I—preparing a solution of at least a salt, that is saturated at a first temperature not lower than room temperature;
- II—mixing said solution with all the oily components of the cream base, at a second temperature higher than said first temperature;
- III—homogenizing and concurrently cooling the complete mixture thus obtained;
- IV—when a third temperature higher than room temperature has been reached, adding the "said salt" solution;
- V—adding fragrances and preservatives;
- VI—mixing additives to form a complete mixture; and
- VII—adding salt in granule form to said complete mixture, while continuing to homogenize said mixture until room temperature is reached.

17. A cosmetic cream consisting of a cream base, at least one solid salt in the form of granules and an aqueous solution containing at least the same salt and saturated with respect to said salt at a temperature not lower than room temperature, wherein said at least one solid salt is selected from the group consisting of sodium chloride, potassium chloride, magnesium chloride and calcium chloride.

18. A cosmetic cream characterized in that it contains at least a solid salt in the form of granules and an aqueous solution containing at least the same salt and saturated with respect to said salt at a temperature not lower than room temperature and a cream base.

19. A cosmetic cream according to claim 18 in which the salt granules are present in an amount of from 5–15% of the total cream.

* * * * *